United States Patent
Reddy et al.

(10) Patent No.: US 6,559,291 B1
(45) Date of Patent: May 6, 2003

(54) PROCESS FOR THE PREPARATION OF DIAZONAPHTHOQUINONESULFONYL-CHLORIDES USING DIPHOSGENE AND TRIPHOSGENE

(75) Inventors: Vummadi Venkat Reddy, Hyderabad (IN); Maruthi Janaki Ram Reddy, Hyderabad (IN); Vaidya Jayathirtha Rao, Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/105,962

(22) Filed: Mar. 25, 2002

(51) Int. Cl.⁷ ............................................. C07C 303/02
(52) U.S. Cl. ...................................... 534/557
(58) Field of Search ......................... 534/557

(56) References Cited

U.S. PATENT DOCUMENTS 6,274,714 B1 * 8/2001 Iida et al. .................. 534/557

OTHER PUBLICATIONS

Chemical Abstracts, 102:113031, 1985.*

* cited by examiner

*Primary Examiner*—Fiona T. Powers
(74) *Attorney, Agent, or Firm*—Ladas & Parry

(57) ABSTRACT

The invention relates to a process for the preparation of diazonaphthoquinonesulfonylchlorides of the formula 1, 2 and 3 using diphosgene or triphosgene.

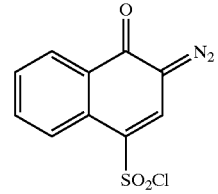

1

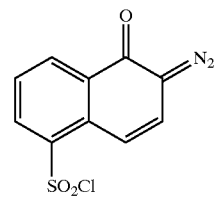

2

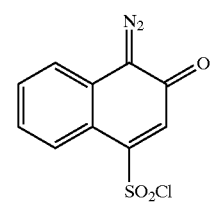

3

10 Claims, No Drawings

PROCESS FOR THE PREPARATION OF DIAZONAPHTHOQUINONESULFONYL-CHLORIDES USING DIPHOSGENE AND TRIPHOSGENE

The present invention relates to a process for the preparation of diazonaphthoquinonesulfonylchlorides, useful intermediates in electronic industry and dye industry. This research pertains to a method of preparation of diazonaphthoquinonesulfonylchlorides having formula 1–3 from corresponding diazonaphthoquinonesulfonic acid or its sodium salt, using diphosgene or triphosgene.

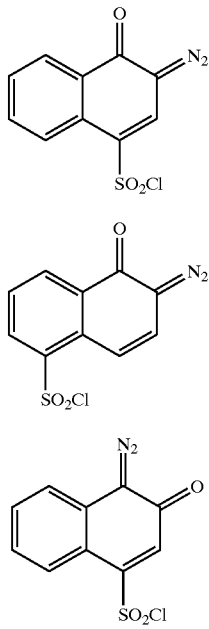

Our interest in preparing these diazonaphthoquinonesulfonylchlorides is to convert them in making various esters and which can be used in formulating the photoresists required for electronics industry.

BACKGROUND OF THE INVENTION

There are a few methods of preparation of diazonaphthoquinonesulfonylchlorides reported in the literature and the same reports will be discussed below with merits and demerits.

The methods reported in prior art on the preparation of diazonaphthoquinonesulfonyl chlorides involves using chlorosulfonic acid and the corresponding diazonaphthoquinone sulfonic acid or its salt (CA, vol. 124, 32490e, PL 161,627, year 1993; CA vol. 64, 2033, USSR 173,756, year 1965; J.Prak.Chem., year 1991, vol. 333, p467). The main disadvantages of this method involves in using excess chlorosulfonic acid, reaction temperature and the evolution of gases like sulfurdioxide and hydrogenchloride.

Another method involves use of thionylchloride with dimethylformamide as catalyst with the corresponding diazonaphthoquinonesulfonic acid or its salt. This method also suffers the disadvantages like heating the reaction mixture, use of excess thionylchloride and evolution of sulfurdioxide and hydrogenchloride gases (CA, vol. 96, 34766b, Khim. Process, year 1981, p505 (Russ)).

Another method involves use of chlorosulfonic acid in combination with thionylchloride along with the corresponding diazonaphthoquinonesulfonic acid or its salt. The main disadvantages are the same as mentioned above (CA, vol. 105, 208620w, Ger (East) 272,511, year 1985 and DD 234,000, year 1986; CA vol. 112, 178384x, Ger (East) DD 269,846, year 1989, Ger (East) 312,180, year 1988; CA, vol. 124, 302642u, JP 08,27,098, year 1996; CA, vol. 125, 170873d, RO 104,624, year 1994).

Yet another method involves is the use of phosgene (toxic gas) with the corresponding diazonaphthoquinonesulfonic acid or its salt. This method has the optimum temperature conditions but the greatest disadvantage is the use of toxic phosgene gas (CA, vol. 102, 113031d, JP 59,196,860, year 1984; CA, vol. 105, 60439w, EP 178,356, year 1986).

SUMMARY OF THE INVENTION

The present invention describes an altogether new process for the preparation of diazonaphthoquinonesulfonylchlorides by reacting the corresponding diazonaphthoquinone sulfonic acid or its salt either with diphosgene or triphosgene in presence of triethylamine base in dichloromethane solvent. Various solvents like chloroform, 1,2-dichloroethane, benzene, toluene, acetonitrile, benzonitrile, nitrobenzene and others are also used. Organic bases like tributylamine, pyridine, tripropylamine, N,N-dimethylaniline, N,N-diethylamine and other bases are also employed. Dichloromethane as solvent and triethylamine as organic base were preferred. The temperature of the reaction was varied over −50 to +5° C. and −40° C. is the preferred temperature condition. The base is found to be essential for the reaction to be conducted and without the organic base there is no reaction occurs. The 2 mole equivalent ratio of base is the right combination found. The work up procedure and isolation of the product diazonaphthoquinonesulfonylchloride is very simple and rapid. After the reaction the organic base and the solvent can be recovered. After the isolation of the product, the remaining filtrate contains the unreacted diazonaphthoquinonesulfonic acid as judged by the UV-Visible absorption data. The products were characterized by the spectral data.

DETAIL DESCRIPTION OF THE INVENTION

Accordingly the present invention provides a process for the preparation of diazonaphthoquinonesulfonylchlorides of formula 1–3, using diphosgene or triphosgene which comprises

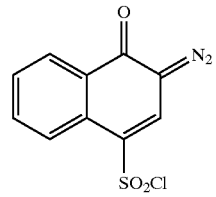

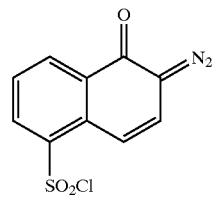

3 reacting diazonaphthoquinonesulfonicacid sodium salt with an organic base in a molar ratio ranging between 1:1.5–1:2.5 in an organic solvent in the presence of diphosgene or triphosgene in a molar ratio of diazonaphthoquinonesulfonicacid sodium salt to diphosgene or triphosgene in the range of 1:1–1:1.5, at a temperature ranging from −50° C. to 5° C., for a period ranging from 40–90 min, subsequently increasing the temperature to 20–25° C., removing the solvent and base from the above said reaction mixture under vacuum to obtain the yellow powder product and re-precipitating the desired product in ice water.

In an embodiment of the present invention the organic base used is selected from the group consisting of triethylamine, tributylamine, pyridine, tripropylamine, N,N-dimethylaniline and N,N-diethylamine.

In an another embodiment the organic base used is triethylamine.

In yet another embodiment the organic solvent used is selected from the group consisting of chloroform, 1,2-dichloroethane, benzene, toluene, acetonitrile, benzonitrile, nitrobenzene and dichloromethane.

In yet another embodiment the organic solvent used is dichloromethane.

In yet another embodiment the molar ratio of diazonaphthoquinonesulfonicacid sodium salt to organic base used is 1:2.

In yet another embodiment the molar ratio of diazonaphthoquinone sulfonicacid sodium salt to triphosgene or diphosgene used is 1:1.

In yet another embodiment A process as claimed in claim 1, wherein the reaction temperature used is −50° C.

In yet another embodiment the diazonaphthoquinonesulfonicacid sodium salt used is selected from 2-Diazo-1-naphthoquinone-4-sulfonic acid sodium salt, 2-Diazo-1-naphthoquinone-5-sulfonic acid sodium salt and 1-Diazo-2-naphthoquinone-4-sulfonic acid sodium salt.

In yet another embodiment the diazonaphthoquinonesulfonyl chloride obtained is selected from 2-Diazo-1-naphthoquinone-4-sulfonylchloride of formula 1, 2-Diazo-1-naphthoquinone-5-sulfonulchloride of formula 2, and 1-Diazo-2-naphthoquinone-4-sulfonylchloride of formula 3.

The following examples are given by way of illustration of the present invention and therefore should not be construed to limit the scope of the present invention.

EXAMPLE 1

2-Diazo-1-naphthoquinone-4-sulfonic acid sodium salt (2.72 g; 0.01 mol) was taken into 25 ml of dichloromethane and cooled to −50° C. Added triethylamine (2.02 g; 0.02 mol) to the above solution and maintained the temperature at −50° C. Then added diphosgene (2.18 g; 0.011 mol) in 15 ml dichloromethane very slowly and maintaining the temperature at −50° C. with stirring over a period of 20 min. The reaction mixture was stirred magnetically for 60 min at −50° C. Reaction mixture was brought to room temperature and then dichloromethane and triethylamine was removed under vacuum. The remaining yellow powder was poured into ice water after 5 min of holding it in ice water the precipitate formed was filtered, washed with ice water and dried in a vacuum desiccator. The dried 2-diazo-1-naphthoquinone-4-sulfonylchloride weight was 2.14 g(0.0080 mol) yield 80% m.p 138–140° C. The 2-diazo-1-naphthoquinone-4-sulfonylchloride was characterized by UV-Visible absorption, $^1$H-nmr and Mass spectrometry.

EXAMPLE 2:

2-Diazo-1-naphthoquinone-4-sulfonic acid sodium salt (10 g; 0.037 mol) was taken into 90 ml of dichloromethane and cooled to −50° C. Added triethylamine (7.4 g; 0.073 mol) to the above solution and maintained the temperature at −50° C. Then added diphosgene (7.35 g; 0.037 mol) in 15 ml dichloromethane very slowly and maintaining the temperature at −50° C. with stirring over a period of 30 min. The reaction mixture was stirred magnetically for 60 min at −50° C. Reaction mixture was brought to room temperature and then dichloromethane and triethylamine was removed under vacuum. The remaining yellow powder was poured into ice water, after 5 min of holding it in ice water the precipitate formed was filtered, washed with ice water and dried in a vacuum desiccator. The dried 2-diazo-1-naphthoquinone-4-sulfonylchloride weight was 7.93 g (0.0296 mol) yield 80%.

EXAMPLE 3

2-Diazo-1-naphthoquinone-5-sulfonic acid sodium salt (2.72 g; 0.01 mol) was taken into 25 ml of dichloromethane and cooled to −50° C. Added triethylamine (2.02 g; 0.02 mol) to the above solution and maintained the temperature at −50° C. Then added diphosgene (2.18 g; 0.011 mol) in 15 ml dichloromethane very slowly and maintaining the temperature at −50° C. with stirring over a period of 20 min. The reaction mixture was stirred magnetically for 60 min at −50° C. Reaction mixture was brought to room temperature and then dichloromethane and triethylamine was removed under vacuum. The remaining yellow powder was poured into ice water, after 5 min of holding it in ice water the precipitate formed was filtered, washed with ice water and dried in a vacuum desiccator. The dried 2-diazo-1-naphthoquinone-5-sulfonylchloride weight was 2.14 g(0.0080 mol) yield 80% mp 135–138° C. The 2-diazo-1-naphthoquinone-5-sulfonylchloride was characterized by UV-Visible absorption, $^1$H-nmr and Mass spectrometry.

EXAMPLE 4

2-Diazo-1-naphthoquinone-5-sulfonic acid sodium salt (10 g; 0.037 mol) was taken into 90 ml of dichloromethane and cooled to −50° C. Added triethylamine (7.4 g; 0.073 mol) to the above solution and maintained the temperature at −50° C. Then added diphosgene (7.35 g; 0.037 mol) in 15 ml dichloromethane very slowly and maintaining the temperature at −50° C. with stirring over a period of 30 min. The reaction mixture was stirred magnetically for 60 min at −50° C. Reaction mixture was brought to room temperature and then dichloromethane and triethylamine was removed under vacuum. The remaining yellow powder was poured into ice water after 5 min of holding it in ice water the precipitate formed was filtered, washed with ice water and dried in a vacuum desiccator. The dried 2-diazo-1-naphthoquinone-5-sulfonylchloride weight was 7.93 g(0.0296 mol) yield 80%.

EXAMPLE 5

1-Diazo-2-naphthoquinone-4-sulfonic acid sodium salt (2.72 g; 0.01 mol) was taken into 25 ml of dichloromethane and cooled to −50° C. Added triethylamine (2.02 g; 0.02 mol) to the above solution and maintained the temperature at −50° C. Then added diphosgene (2.18 g; 0.011 mol) in 15 ml dichloromethane very slowly and maintaining the temperature at −50° C. with stirring over a period of 20 min. The reaction mixture was stirred magnetically for 60 min at −50° C. Reaction mixture was brought to room temperature and then dichloromethane and triethylamine was removed under vacuum. The remaining yellow powder was poured into ice water, after 5 min of holding it in ice water the precipitate formed was filtered, washed with ice water and dried in a vacuum desiccator. The dried 1-diazo-2-naphthoquinone-4-sulfonylchloride weight was 2.14 g(0.0080 mol) yield 80%, m.p 138–140° C. The 1-diazo-2-naphthoquinone-4-sulfonylchloride was characterized by UV-Visible absorption, $^1$H-nmr and Mass spectrometry.

Example 6

2-Diazo-1-naphthoquinone-4-sulfonic acid sodium salt (2.72 g; 0.01 mol) was taken into 25 ml of dichloromethane and cooled to −50° C. Added triethylamine (2.02 g; 0.02 mol) to the above solution and maintained the temperature at −50° C. Then added triphosgene (3.2 g; 0.011 mol) in 15 ml dichloromethane very slowly and maintaining the temperature at −50° C. with stirring over a period of 20 min. The reaction mixture was stirred magnetically for 60 min at −50° C. Reaction mixture was brought to room temperature and then dichloromethane and triethylamine were removed under vacuum. The remaining yellow powder was poured into ice water, after 5 min of holding it in ice water the precipitate formed was filtered, washed with ice water and dried in a vacuum desiccator. The dried 2-diazo-1-naphthoquinone-4-sulfonylchloride weight was 2.14 g (0.0080 mol) yield 80%.

EXAMPLE 7

2-Diazo-1-naphthoquinone-5-sulfonic acid sodium salt (2.72 g; 0.01 mol) was taken into 25 ml of dichloromethane and cooled to −50° C. Added triethylamine (2.02 g; 0.02 mol) to the above solution and maintained the temperature at −50° C. Then added triphosgene (3.2 g; 0.011 mol) in 15 ml dichloromethane very slowly and maintaining the temperature at −50° C. with stirring over a period of 20 min. The reaction mixture was stirred magnetically for 60 min at −50° C. Reaction mixture was brought to room temperature and then dichloromethane and triethylamine were removed under vacuum. The remaining yellow powder was poured into ice water, after 5 min of holding it in ice water the precipitate formed was filtered, washed with ice water and dried in a vacuum desiccator. The dried 2-diazo-1-naphthoquinone-5-sulfonylchloride weight was 2.14 g (0.0080 mol) yield 80%.

EXAMPLE 8

1-Diazo-2-naphthoquinone-4-sulfonic acid sodium salt (2.72 g; 0.01 mol) was taken into 25 ml of dichloromethane and cooled to −50° C. Added triethylamine (2.02 g; 0.02 mol) to the above solution and maintained the temperature −50° C. Then added triphosgene (3.2 g; 0.011 mol) in 15 ml dichloromethane very slowly and maintaining the temperature −50° C. with stirring over a period of 20 min. The reaction mixture was stirred magnetically for 60 min at −50° C. Reaction mixture was brought to room temperature and then dichloromethane and triethylamine was removed under vacuum. The remaining yellow powder was poured into ice water, after 5 min of holding it in ice water the precipitate formed was filtered, washed with ice water and dried in a vacuum desiccator. The dried 1-diazo-2-naphthoquinone-4-sulfonylchloride weight was 2.14 g (0.0080 mol) yield 80%.

Advantages:

The various advantages of this process methodology is given below:

The main advantage of this method is that the very mild experimental conditions are well tuned and defined to get very good yields.

The advantage of this method is that the reaction temperature is defined around −50° C. to 0° C. (preferably at −40° C.).

The advantage of this method is that the use of diphosgene/triphosgene novel reagents compared to toxic phosgene gas.

The main advantage of this method is that there are no evolutions of corrosive gases like $SO_2$ and HCl making it environment friendly.

The advantage of this method is that use of diphosgene/triphosgene (of 1.1 equivalents) is just optimum compare to other reported procedures, where phosgene, chlorosulfonicacid & thionylchloride employed are in excess.

The advantage of this method is that it requires only two equivalents of triethylamine to conduct the reaction.

The advantage of this method is that the organic base triethylamine used can be recovered

We claim:

1. A process for the preparation of diazonaphthoquinone-sulfonylchlorides of formula 1, 2 and 3 using diphosgene or triphosgene which comprises

1

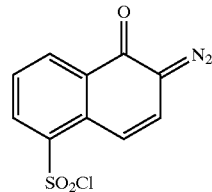

2

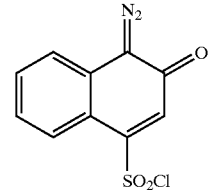

3 reacting diazonaphthoquinonesulfonicacid sodium salt with an organic base in a molar ratio ranging between 1:1.5–1:2.5 in an organic solvent in the presence of diphosgene or triphosgene in a molar ratio of diazonaphthoquinonesulfonicacid sodium salt to diphosgene or triphosgene in the range of 1:1–1:1.5, at a temperature ranging from −50° C. to 5° C., for a period ranging from 40–90 min, subsequently increasing the temperature to 20–25° C. and removing the solvent and base from the above said reaction mixture under vacuum to obtain the yellow powder product and re-precipitating the desired product in ice water.

2. A process as claimed in claim 1, wherein the organic base used is selected from the group consisting of triethylamine, tributylamine, pyridine, tripropylamine, N,N-dimethylaniline and N,N-diethylamine.

3. A process as claimed in claim 2, wherein the organic base used is preferably triethylamine.

4. A process as claimed in claim 1, wherein the organic solvent used is selected from the group consisting of chloroform, 1,2-dichloroethane, benzene, toluene, acetonitrile, benzonitrile, nitrobenzene and dichloromethane.

5. A process as claimed in claim 2 wherein the organic solvent used is preferably dichloromethane.

6. A process as claimed in claim 1, wherein the molar ratio of diazonaphthoquinonesulfonicacid sodium salt to organic base used is preferably 1:2.

7. A process as claimed in claims 1, wherein the molar ratio of diazonaphthoquinone sulfonicacid sodium salt to triphosgene or diphosgene used is preferably 1:1.

8. A process as claimed in claims 1, wherein the reaction temperature used is preferably −50° C.

9. A process as claimed in claims 1, wherein the diazonaphthoquinonesulfonicacid sodium salt used is selected from 2-Diazo-1-naphthoquinone-4-sulfonic acid sodium salt, 2-Diazo-1-naphthoquinone-5-sulfonic acid sodium salt and 1-Diazo-2-naphthoquinone-4-sulfonic acid sodium salt.

10. A process as claimed in claims 1, wherein the diazonaphthoquinonesulfonyl chloride obtained is selected from 2-Diazo-1-naphthoquinone-4-sulfonylchloride of formula 1, 2-Diazo-1-naphthoquinone-5-sulfonylchloride of formula 2, and 1-Diazo-2-naphthoquinone-4-sulfonylchloride of formula 3.

* * * * *